United States Patent [19]

Spry

[11] 3,933,806

[45] Jan. 20, 1976

[54] CEPHALOSPORIN MICHAEL ADDUCTS

[75] Inventor: Douglas O. Spry, Indianapolis, Ind.

[73] Assignee: Eli Lilly and Company, Indianapolis, Ind.

[22] Filed: July 17, 1973

[21] Appl. No.: 380,011

[52] U.S. Cl. .............................. 260/243 C; 424/246
[51] Int. Cl.² ........................................ C07D 501/20
[58] Field of Search ................................. 260/243 C

[56] References Cited
UNITED STATES PATENTS 3,660,395  5/1972  Wright et al. .................... 260/243 C
3,660,396  5/1972  Wright ........................... 260/243 C

*Primary Examiner*—Nicholas S. Rizzo
*Attorney, Agent, or Firm*—James L. Rowe; Everet F. Smith

[57] ABSTRACT

7-Acylamino-2-(substituted ethyl)-3-(substituted alkyl)-3-cephem-4-carboxylic acids and esters are prepared via carbanion addition to 2-methylene-3-cephem sulfoxides to provide antibiotic cephalosporin Michael adducts.

13 Claims, No Drawings

CEPHALOSPORIN MICHAEL ADDUCTS

BACKGROUND OF THE INVENTION

In the chemical modifications of cephalosporin antibiotics, another type of substitution at carbon atom C-2 of the 3-cephem moiety was discovered when a cephalosporin was reacted under Mannich conditions to give a product which did not contain the usual β-substituted amino group of the normal Mannich reaction products. The identification of a methylene group at C-2 indicated that the expected amino group had been eliminated under reaction conditions. The cephalosporin exocyclic methylene at C-2 was found to undergo certain addition reactions. Bromine and thiols were added under mild conditions. However, amines or alcohols did not add to the double bond under the conditions studied.

It has been found that certain carbanions will undergo a Michael type addition with 2-methylene-3-cephem sulfoxides to provide novel cephalosporin Michael adducts which have antibiotic properties.

It is an object of this invention to provide antibiotic 7-acylamino-2-(substituted ethyl)-3-cephem-4-carboxylic acids which are prepared with the 2-methylene cephalosporins available by the method of Wright, et al., *J. Med. Chem.*, 14, 420 (1971).

In the chemical modification of cephalosporins, it is often desirable to cleave the 7-carboxamido group to obtain a free amino group in the 7-position. One method of cleaving an amido group to obtain the free amine is that described by Lander, *J. Chem. Soc.*, 83, 320 (1903). In accordance with Lander's method the amide is treated with a halogenating agent to convert the amido group to an imino halide and the imino halide is treated with an alcohol to obtain the imimo ether which is then hydrolyzed to the free amine. The application of this method to the cleavage of cephalosporin C to 7-aminocephalosporanic acid (7-ACA) is disclosed in Canadian Pat. No. 770,125 and British Pat. No. 1,041,985.

Cleavage of the carboxamido group of the 7-acylamino-2-(substituted ethyl) cephalosporins of this invention provides the 7-amino-2-(substituted ethyl)-3-cephem compounds described herein. Such a cephalosporin Michael adduct "nucleus" is useful for generating further 7-acylamino-2-(substituted ethyl) cephalosporins of this invention.

SUMMARY OF THE INVENTION

The compounds provided by this invention are represented by the following formula,

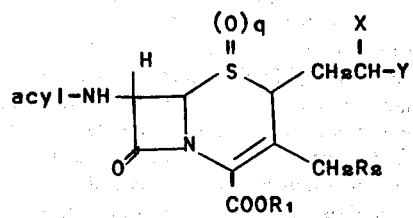

wherein the term "acyl" represents a wide variety of known side chains of the cephalosporin antibiotics such as phenylacetyl, phenylmercaptoacetyl, phenylglycyl, mandelyl, and the like; $R_1$ represents hydrogen, an alkali or alkaline earth metal cation or an anhydride- or ester-forming moiety and preferably one which is easily removed so as to provide the carboxylic acid form of the desired antibiotic; $R_2$ represents hydrogen, $C_2$-$C_5$ alkanoyloxy, or $C_1$-$C_4$ alkoxy, X and Y independently represent hydrogen, acetyl, benzoyl, carboethoxy, carbomethoxy, cyano, nitro or 2,2,2-trichlorocarboethoxy, with the limitation that when one of X or Y is hydrogen, the other is cyano or nitro. The symbol q is 0 to 1 indicating the sulfide or sulfoxide state of the sulfur atom in the dihydrothiazine ring. As used herein the term "cephalosporin," refers to those compounds having the 3-cephem ring structure and includes 3-methyl-3-cephem compounds (the deacetoxy cephalosporanic acids), the 3-acetoxymethyl-3-cephem compounds (the cephalosporanic acids), and 3-(alkoxymethyl)-3-cephem derivatives.

The term "Michael adduct" or "cephalosporin Michael adduct" refers to the 2-(substituted ethyl)-3-cephem compounds obtained by reacting a 2-methylene-3-cephem sulfoxide with a methylene carbanion of the formula, —CHXY, via a Michael type addition to the C-2 exomethylene double bond, and to the products derived therefrom The compounds of the invention exhibit the usual infrared absorption exhibited by the unsubstituted cephalosporanic acids. In addition the cephalosporin Michael adducts exhibit the proton magnetic resonance spectra (NMR) characteristic of the methylene adduct.

The cephalosporin Michael adducts, the 2-(substituted methylene)-3-cephem compounds, provided by this invention inhibit the growth of gram-positive pathogenic organisms.

DETAILED DESCRIPTION

The cephalosporin Michael adducts of the present invention are represented by Formula I

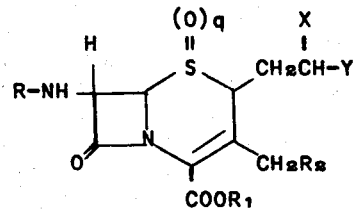

wherein R is hydrogen, $C_1$-$C_8$ alkanoyl, benzoyl, or a group represented by the formula:

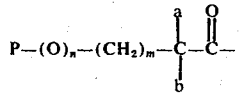

wherein P is 2-thienyl, 3-thienyl, 2-furyl, 3-furyl, phenyl or phenyl substituted by amino, protected amino, halogen, hydroxy, protected hydroxy, $C_1$-$C_4$ lower alkyl, or $C_1$-$C_4$ lower alkoxy;

*a* is hydrogen or $C_1$-$C_3$ alkyl;

*b* is hydrogen, $C_1$-$C_3$ alkyl, amino, protected amino, hydroxy, or protected hydroxy;

*m* is 0 or an integer from 1 to 3;

*n* is 0 or 1;

subject to the limitation that when n is 1, P is phenyl or substituted phenyl and *b* is hydrogen or $C_1$-$C_3$ alkyl;

R₁ is hydrogen, a carboxylic acid protecting group, or an alkali metal or alkaline earth metal cation;

R₂ is hydrogen, $C_2$-$C_5$ alkanoyloxy, or $C_1$-$C_4$ alkoxy;

q is 0 or 1; and

X and Y are independently hydrogen, acetyl, benzoyl, carboethoxy, carbomethoxy, cyano, nitro or 2,2,2-trichlorocarboethoxy;

subject to the limitations that when one of X and Y is hydrogen, the other is cyano or nitro.

As used herein, the term "$C_1$-$C_8$ alkanoyl" refers to formyl, acetyl, propionyl, butyryl, pivaloyl, hexanoyl, heptanoyl and like groups represented by the formula

where R₄ is hydrogen or a straight or branched chain alkyl group having from 1 to 7 carbon atoms.

Representative of the 7-acyl group R, when R is

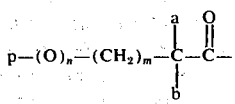

are phenylacetyl, phenoxyacetyl, 2-thienylacetyl, 3-thienylacetyl, 2-furylacetyl, 3-furylacetyl, 4-methylphenylacetyl, 4-methoxy-3-ethoxyphenylacetyl, phenylglycyl, β-phenylpropionyl, α-methylphenylacetyl, α,α-dimethylphenylacetyl, α-hydroxyphenylacetyl, α-n-propylphenylacetyl, 3-hydroxyphenylacetyl, 4-hydroxyphenylacetyl, 3-hydroxyphenylglycyl, 4-hydroxyphenylglycyl, 4-t-butylphenoxyacetyl, 3-phenoxypropionyl, 4-chlorophenoxyacetyl, 4-phenylbutyryl, 4-phenoxybutyryl, 5-phenylvaleryl, 5-phenoxyvaleryl, 3-bromophenoxyacetyl, α-aminothienylacetyl, and like 7-acyl groups.

With reference to phenyl substituents, such substituent groups can occupy any available position on the benzene ring. Phenyl substituted by amino refers to phenyl substituted by one or more amino or protected amino substituents. Exemplary of such amino or protected amino-substituted groups are 3-aminophenyl, 4-aminophenyl, 2-benzyloxycarbonylaminophenyl, 3-formylaminophenyl, 4-t-butyloxycarbonylaminephenyl and the like. Preferred substituents are the 3-aminophenyl and 4-aminophenyl. Phenyl substituted by $C_1$-$C_4$ lower alkyl refers to phenyl substituted by one or more methyl, ethyl, n-propyl, isopropyl, n-butyl, sec-butyl, isobutyl and t-butyl substituents. Exemplary of such lower alkyl substituted groups are 4-t-butylphenyl, 3,4-dimethylphenyl, 4-ethylphenyl, 4-isopropylphenyl, 2-methylphenyl and the like. Preferred substituents are the 3-methylphenyl, 4-methylphenyl and 3,4-dimethylphenyl. Phenyl substituted by $C_1$-$C_4$ lower alkoxy refers to phenyl substituted by one or more butoxy, ethoxy, methoxy, and propoxy substituents. Exemplary of such $C_1$-$C_4$ lower alkoxy substituted groups are 4-t-butoxyphenyl, 3-ethoxyphenyl, 2-methoxyphenyl, 3-isopropoxyphenyl, 3-methoxy-4-ethoxyphenyl, 3,4-dimethoxyphenyl and the like. Preferred substituents are the 3-methoxyphenyl, 4-methoxyphenyl and 3,4-dimethoxyphenyl. Halophenyl refers to phenyl substituted by one or more bromo, chloro or fluoro substituents. Exemplary of such halogen substituted groups are 2-bromophenyl, 3-chlorophenyl, 4-fluorophenyl and 3,4-dichlorophenyl and the like. Preferred substituents are the 3-chlorophenyl, 4-chlorophenyl and 3,4-dichlorophenyl. Phenyl substituted by hydroxy refers to phenyl substituted by one or more hydroxy or protected hydroxy substituents. Exemplary of such hydroxy or protected hydroxy-substituted groups are 3-hydroxyphenyl, 4-hydroxyphenyl, 3,4-dihydroxyphenyl, 4-t-butyloxycarbonyloxyphenyl, 2-formyloxyphenyl, 3,4-bis(benzyloxy)phenyl, 3-benzhydryloxyphenyl and the like. Preferred substituents are the 3-hydroxyphenyl, 4-hydroxyphenyl and 3,4-dihydroxyphenyl.

In the following description, amino, carboxy and hydroxy protecting groups are not exhaustively defined. The function of such groups is to protect the reactive functional groups during the preparation and then be easily removed without disrupting the remainder of the molecule. Many such protecting groups are well known in the art, and the use of other groups, not specifically listed, will be recognized as suitable.

With reference to R₁ in the above formula, a "carboxylic acid protecting group" refers to the organic ester or anhydride forming radicals which are commonly employed in the protection of the carboxylic acid function of the penicillin and cephalosporin antibiotics and more generally for the protection of the carboxylic acid function of amino acids and peptides. Such protecting groups are those which are stable under the conditions of the reaction but are susceptible to cleavage under acid or base hydrolytic or hydrogenolytic conditions. The specific carboxylic acid protecting groups employed are not material to the present invention so long as the foregoing criteria of stability under the reaction conditions and ease of cleavage are fulfilled. Many such groups, other than those specifically exemplified herein are well known to those skilled in the art. R₁, therefore, can be an ester-forming group which protects the reactive carboxyl group during the various chemical operations employed. Exemplary of such ester forming groups are t-butyl, benzyl, benzhydryl, 3,5-dimethoxybenzyl, p-methoxybenzyl, 4-methoxybenzhydryl, p-nitrobenzyl, phenacyl, p-bromophenacyl, 2,2,2-trichloroethyl, tetrahydropyranyl and the like. R₁ can also be the acyl radical derived from an acid and affording protection of the carboxyl group by anhydride formation. Thus, R₁ can be the acyl radical

wherein R₅ is $C_1$-$C_8$ alkyl; halo $C_1$-$C_8$ alkyl; or —Y—$(CH_2)_n$— wherein Y is oxygen, sulfur, or methylene; and n is an integer from 0 to 3. The resulting anhydride is a mixed anhydride comprising the carboxyl group of the cephalosporin and the acyl radical from the acid R₅COOH. Examples of suitable mixed anhydrides include those derived from acetic acid, chloroacetic acid, propionic acid, valeric acid, phenylacetic acid, phenoxyacetic acid, and benzoic acid. The acetic and propionic mixed anhydrides are preferred because of their ease of preparation. Other mixed anhydrides not specifically named are equivalent and will perform the same blocking function as those named. When R₁ is an alkali or alkaline earth metal cation such cations as the lithium, sodium, potassium and calcium cations are representative.

The term "protected amino" as used herein refers to a primary amino group substituted by an amide or enamine forming radical which is commonly employed in the protection of the amino function of the penicillin and cephalosporin antibiotics and more generally for the protection of the amino function of amino acids and peptides. Such amino protecting or blocking groups are those which are stable under the conditions of the reaction but are susceptible to cleavage ("deblocking") under acid hydrolytic or hydrogenolytic conditions. The specific amino protecting group employed is not material so long as the foregoing criteria of stability under the reaction conditions and ease of cleavage are fulfilled. Many such groups, other than those specifically exemplified herein are well known to those in the art. Exemplary of such amide and enamine forming radicals are t-butyloxycarbonyl, benzyloxycarbonyl, substituted benzyloxycarbonyl, 2,2,2-trichloroethyloxycarbonyl, adamantyloxycarbonyl, trifluoroacetyl, chloroacetyl, ethyl acetoacetate, pentane-1,3-dione, phthaloyl, formyl and the like. It may be necessary to protect the reactive amino substituents on both the phenyl moiety and on the α-carbon atom on the 7-acyl moiety represented by $b$ in Formula I and it will be recognized by those familiar with the art that the choice of amino protecting group may be dependent upon the type of amino group encountered.

The term "protected hydroxy" refers to a hydroxyl group substituted by an ether or ester forming radical which is commonly employed in the protection of the reactive hydroxyl function in the antibiotic and peptide arts. Such hydroxy protecting or blocking groups are those which are stable under the reaction conditions but are susceptible to cleavage ("deblocking") under acid or base hydrolytic or hydrogenolytic conditions. The specific hydroxyl protecting group employed is not material so long as the foregoing criteria of stability and ease of cleavage are fulfilled. Exemplary of such hydroxyl ether and ester-forming radicals are benzyl, benzhydryl, t-butyloxycarbonyl, benzyloxycarbonyl, 2,2,2-trichloroethoxycarbonyl, formyl, ethylvinyl and the like.

Protection of co-existing amino and hydroxyl groups is possible with the same or different "blocking groups." Also, selective removal or "deblocking" is possible under certain conditions and is well within the skill of those versed in the art.

The compounds of the present invention are prepared by reacting a 2-methylene-3-cephem sulfoxide represented by Formula II with a molar equivalent of a methylene carbanion, —CHXY, generated in an inert solvent from an active methylene component of the formula, $XCH_2Y$, in the presence of a base. The substituent groups R′ and R′$_1$ have the same meaning as R and R$_1$ respectively, other than hydrogen. Hereinafter R′ and R′$_1$ include the respective definitions of R and R$_1$, R′ and R′$_1$ being other than hydrogen.

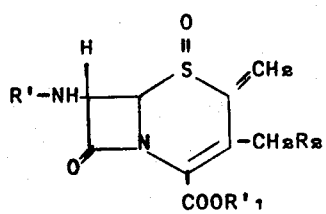

The active methylene components which are suitable for the Michael addition are acetonitrile, acetylacetone(2,4-pentanedione), acetoacetic esters, benzoylacetone, benzoylacetic esters, cyanoacetic esters, cyanoacetone, cyanoacetophenone, dibenzoylmethane(1,3-diphenyl-1,3-propanedione), malonic esters, malononitrile, nitromethane and the like.

Bases strong enough to generate a methylene carbanion such as n-butyl lithium, lithium diisopropylamide, sodium hydride, sodium hydroxide, sodium methoxide, benzyltrimethylammonium hydroxide and the like are employed.

This invention also concerns the process for preparing the compounds of Formula I, wherein R and R$_1$ are other than hydrogen and q is 1, which comprises reacting in a substantially anhydrous inert solvent at a temperature between −40°C. and 20°C., a compound of the Formula II with a carbanion of the formula, —CHXY, generated from an active methylene component of the formula, $XCH_2Y$, in the presence of a base, wherein X and Y are defined hereinabove.

Solvents which may be employed in the present invention are any commonly used reaction solvents which are unreactive with the starting materials and products and are preferably those which do not undergo carbanionic reactions. In general, any solvent in which the starting material is at least partially soluble at the addition temperature and which is unreactive with the reaction mixture constituents can be employed. Exemplary of the solvents which are employed are dimethylacetamide (DMAC), dimethylformamide (DMF), dichloroethane, tetrahydrofuran, dioxane and other ethers, for example, the dimethylether of ethyleneglycol.

The 2-methylene-3-cephem sulfoxides of the Formula II, the starting materials for the present invention, are prepared according to known reactions. The compounds of Formula II are prepared by treating a cephalosporin ester sulfoxide with aqueous formaldehyde and a variety of amine salts under Mannich conditions to form the expected Mannich product as an intermediate. The Mannich reaction product is unstable under the reaction conditions and loses the amine to give a methylene compound of the Formula II. The methods and procedures for the Mannich reaction are described by Wright, et al., *J. Med. Chem.* 14, 420 (1971).

A compound represented by Formula I, wherein q is 1, is prepared by reacting a 2-methylene-3-cephem sulfoxide represented by the Formula II with a methylene carbanion of the formula, —CHXY, in an anhydrous inert solvent via addition of the carbonion across the methylene double bond. Generally, the carbanion is generated in situ for convenience and is preferably employed in excess. The reaction may be carried out conveniently at or about 0°C.; however, the addition occurs at a temperature of from about −40°C. to about 20°C.

Preferably between 1.0 and 1.1 moles of carbanion per mole of 2-methylene-3-cephem sulfoxide is generated in situ with the use of a base such as sodium hydride on a suitable active methylene component in an inert solvent. the active methylene component has the formula, $XCH_2Y$, wherein X and Y are independently hydrogen, acetyl, benzoyl, carboethoxy, carbomethoxy, cyano, nitro or 2,2,2-trichlorocarboethoxy and when one of X and Y is hydrogen, the other is cyano or nitro. Preferably dimethylformamide is employed as a solvent for the addition of starting materials and the amount thereof is not critical.

In a preferred embodiment of this invention, a solution of 2,2,2-trichloroethyl 3-methyl-2-methylene-7-phenoxyacetamido-3-cephem-4-carboxylate sulfoxide in DMF is added dropwise under nitrogen, to a DMF solution of the carbanion generated from dimethyl malonate and sodium hydride. The reaction is continued for about an hour at 0°C. under nitrogen. The reaction mixture is decomposed with dilute hydrochloric acid solution. The reaction mixture is taken up in ethyl acetate, washed, dried and evaporated to dryness. The residue is chromatographed to yield 2,2,2-trichloroethyl 2-(2,2-dimethoxycarbonylethyl)-3-methyl-7-phenoxyacetamido-3-cephem-4-carboxylate sulfoxide.

In another embodiment of the present invention, a solution of 2,2,2-trichloroethyl 3-acetoxymethyl-2-methylene-7-[2-(2-thienyl) acetamido]-3-cephem-4-carboxylate sulfoxide in DMF is added dropwise under nitrogen, to a DMF solution of the carbanion generated from dimethyl malonate and sodium hydride. The reaction is continued for about an hour at 0°C. under nitrogen. The reaction mixture is decomposed with sodium chloride solution. The reaction mixture is taken up in ethyl acetate, washed, dried and evaporated to dryness. The residue is chromatographed to yield 2,2,2-trichloroethyl 3-acetoxymethyl-2-(2,2-dimethoxycarbonylethyl)-7-[(2-thienyl)acetamido]3-cephem-4-carboxylate sulfoxide.

In a further embodiment of the instant invention, a solution of 2,2,2-trichloroethyl 3-acetoxymethyl-2-methylene-7-[(2-thienyl) acetamido]-3-cephem-4-carboxylate sulfoxide in DMF is added dropwise under nitrogen, to a DMF solution of the carbanion generated from ethyl acetoacetate and sodium hydride. The reaction is continued for about an hour at 0°C. under nitrogen. The reaction mixture is decomposed with sodium chloride solution. The reaction mixture is taken up in ethyl acetate, washed, dried and evaporated to dryness. The residue is chromatographed to yield 2,2,2-trichloroethyl 3-acetoxymethyl-2-(2-acetyl-2-ethoxycarbonylethyl)-7-[(2-thienyl) acetamido]-3-cephem-4-carboxylate sulfoxide.

In another embodiment of the present invention, the 7-amino-2-(substituted ethyl) cephalosporins of Formula I, wherein R and $R_1$ are hydrogen, are prepared from a compound represented by Formula I, wherein R is an acyl group and 9 is o, by cleavage of the 7-carboxamido group. The 7-carboxamido group is cleaved by blocking the carboxyl of the 2-(substituted ethyl) cephalosporin acid by conversion to a mixed anhydride as described by Chauvette et al., *J. Antibiot.*, 248 (1972), treating the blocked cephalosporin with a halogenating agent to convert the amido group to an imino halide, treating the imino halide with an alcohol to obtain an imino ether, and hydrolyzing the imino ether to give a free 7-amino group with concomitant removal of the blocking group.

The 2-(substituted ethyl)-3-cephem compounds provided by this invention are converted to 2-(substituted ethyl)-3-cephem 4-carboxylic acids according to methods well known to those skilled in the art. The 2-(substituted ethyl)-3-cephem sulfoxide esters represented by Formula I, wherein q is 1, are reduced via a trivalent phosphorus compound as described in U.S. Pat. No. 3,641,014 for example. The reduction products, the 2-(substituted ethyl)-3-cephem-4-carboxylic esters, are converted to the corresponding 2-(substituted ethyl)-3-cephem-4-carboxylic acids by cleavage of the ester groups, for example, with zinc dust in acetic acid as described by Woodward et al., *J. Amer. Chem. Soc.* 88, 852 (1966) or with trifluoroacetic acid in anisole or by hydrogenolysis with palladium on carbon to provide the compounds of Formula I, wherein $R_1$ is hydrogen and $q$ is 0.

The following reaction scheme illustrates the procedures employed in this invention and illustrates further the usefulness of the invention for converting 2-methylene cephalosporins into cephalosporin Michael adducts via the intermediates described.

Reaction Scheme

Cephalosporin Michael Adducts

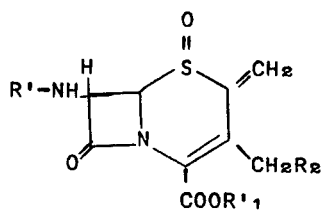

↓ 1)   -CHXY (carbanion addition)

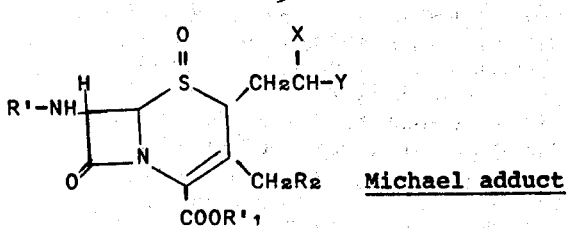

Michael adduct

2) Sulfoxide reduction
2a) Amide cleavage (alternate)
3) Ester cleavage

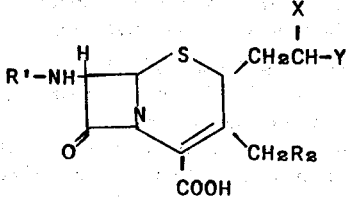

The instant Michael adduct cephalosporin acids inhibit the growth of gram-positive organisms at concentrations as low as 1 milligram per milliliter in the standard agar dilution test as measured by zone inhibition against *Staphylococcus aureus* (SA), *Bacillus subtilis* (X12), *Sarcina lutea* (X186) and *Mycobacterium avium* (X85). Typical of the gram-positive activities of such 2-(substituted ethyl)-3-cephem-4-carboxylic acids expressed as organism/Zone inhibition (diameter, mm) are the following: 2-(2,2-dimethoxylcarbonylethyl)-3-methyl-7-phenoxyacetamido-3-cephem-4-carboxylic acid, SA/19, X12/23 and X186/13; 3-acetoxymethyl-2-[2,2-dimethoxycarbonylethyl]-7-[2-(2-thienyl)acetamido]-3-cephem-4-carboxylic acid, SA/28, X12/28, X85/19 and X186/28; 3-acetoxymethyl-2-(2-acetyl-2-ethoxycarbonylethyl)-7-[2-(2-thienyl)acetamido]-3-cephem-4-carboxylic acid, SA/30, X12/31, X85/21 and X186/29.

The 3-cephem-4-carboxylic acid Michael adducts are useful in combatting gram-positive microbial infections in warm-blooded animals. When administered parenterally at a non-toxic dose between about 50 and 500 mg./kg. of body weight, the compounds of the invention are effective in controlling bacterial infections in warm-blooded mammals. The compounds can be administered as a single dose or as multiple daily doses, dependent upon such conditions as the general health of the host and the type and severity of the infection. A compound of the invention can be administered as a single daily dose which regimen may be continued until the desired therapeutic result is achieved. Alternatively, a treatment employing multiple doses, for example, 3 or 4 doses administered daily, may be used with a particular host.

Illustrative of the 2(substituted methylene)-3-cephem carboxylic acids and esters which are provided by this invention are the following:

benzyl 2-(2,2-diacetylethyl)-3-methyl-7-acetamido-3-cephem-4-carboxylate sulfoxide benzhydryl 2-(2-acetyl-2-benzoylethyl)-3-methoxymethyl-7-pivalamido-3-cephem-4-carboxylate sulfoxide t-butyl 7-formamide-2-(2-acetyl-2-methoxycarbonylethyl)-3-valeryloxymethyl-3-cephem-4-carboxylate sulfoxide 3,5-dimethoxybenzyl 7-acetamido-2-(2-acetyl-2-ethoxycarbonylethyl)-3-isopropoxymethyl-4-cephem carboxylate sulfoxide p-nitrobenzyl 3-acetoxymethyl-7-[(3-hydroxyphenyl)acetamido]-2-[2-acetyl-2(2,2,2-trichloroethoxycarbonyl)ethyl]-3-cephem-4-carboxylate sulfoxide 2,2,2-trichloroethyl 3-butoxymethyl-7-[(4-methoxyphenyl)acetonitrile]-2-(2-acetyl-2-cyanoethyl)-3-cephem-4-carboxylate sulfoxide benzyl 3-methyl-2-(2,2-dibenzoylethyl)-7-[(4-methylphenyl)acetamido]-3-cephem-4-carboxylate sulfoxide benzhydryl 3-isopropoxymethyl-2-(2-benzoyl-2-methoxylcarbonylethyl)-7-($\alpha$-methylphenylacetamido)-3-cephem-4-carboxylate t-butyl 7-($\alpha,\alpha$-dimethylphenylacetamido)-3-ethoxymethyl-2-(2-benzoyl-2-ethoxycarbonylethyl)-3-cephem-4-carboxylate 3,5-dimethoxybenzyl 3-acetoxymethyl-7-[($\alpha$-n-propyl)phenylacetamido]-2-[2-benzoyl-2(2,2,2-trichloroethoxycarbonyl)ethyl]-3-cephem-4-carboxylate p-nitrobenzyl 2-(2-benzoyl-2-cyanoethyl)-7-(4-phenylbutyramido)-3-propionyloxymethyl-3-cephem-4-carboxylate 2,2,2-trichloroethyl 3-butyryloxymethyl-2-(2,2-dimethoxycarbonylethyl)-7-(5-phenylvaleramido)-3-cephem-4-carboxylate 3-acetoxymethyl-7-phenoxyacetamido-2-(2-ethoxycarbonyl-2-methoxycarbonylethyl)-3-cephem-4-carboxylic acid 3-methyl-7-(5-phenoxyvaleramido)-2-[2-methoxycarbonyl-2-(2,2,2-trichloroethoxycarbonyl)ethyl]-3-cephem-4-carboxylic acid 7-(4-chlorophenoxy)acetamido-3-methyl-2-(2-cyano-2-methoxycarbonylethyl)-3-cephem-4-carboxylic acid 3-methoxymethyl-2-(2,2-diethoxycarbonylethyl)-7-[(2-thienyl)acetamido]-3-cephem-4-carboxylic acid lithium salt 7-[$\alpha$-amino-(2-thienyl)acetamido]-3-methyl-2-[2-ethoxylcarbonyl-2-(2,2,2-trichloroethoxycarbonyl)ethyl]-3-cephem-4-carboxylic acid 7-glycylamido-2-(2-cyano-2-methoxycarbonylethyl)-3-propoxymethyl-3-cephem-4-carboxylic acid 7-(2-furyl)acetamido-3-methyl-2-(2,2-dicyanoethyl)-3-cephem-4-carboxylic acid potassium salt 3-acetoxymethyl-7-(N-benzoyloxycarbonylglycylamido)-2-[2-cyano-2-(2,2,2-trichloroethoxycarbonyl)ethyl]-3-cephem-4-carboxylic acid sodium salt 7-(N-t-butyloxycarbonylglycylamido)-3-isopropoxymethyl-2-[2,2-bis(2,2,2-trichloroethoxycarbonyl)ethyl]-3-cephem-4-carboxylic acid 2,2,2-trichloroethyl 3-acetoxymethyl-2-(2-nitroethyl)-7-phenoxypropionamido-3-cephem-4-carboxylate sulfoxide p-nitrobenzyl 2-(2-cyanoethyl)-3-methyl-7-[(2-thienyl)-acetamido]-4-carboxylic acid 2,2,2-trichloroethyl 3-acetoxymethyl-2-(2-acetyl-2-methoxycarbonylethyl)-7-(N-2,2,2-trichloroethoxycarbonylglycylamido)-3-cephem-4-carboxylate 7-(O-benzylmandelamido)-2-(2-cyanoethyl)-3-methyl-3-cephem-4-carboxylic acid 2,2,2-trichloroethyl 7-(O-formylmandelamido)-3-methyl-2-(2,2-diacetylethyl)-3-cephem-4-carboxylate acetic 3-acetoxymethyl-2-(2,2-dimethoxycarbonylethyl)-7-phenoxyacetamido-3-cephem-4-carboxylic anhydride propionic 3-methyl-7-[(2-thienyl)acetamido]-2-[2,2-bis(2,2,2-trichloroethoxycarbonyl)ethyl-3-cephem-4-carboxylic anhydride The cephalosporin acids of this invention readily form salts such as the lithium, sodium and potassium salts by reaction of the free antibiotic acid in a suitable solvent with an alkali metal carbonate or bicarbonate. The alkaline earth salts such as calcium and barium are prepared in similar manner.

The compounds of the invention, represented by the Formula I, which are esters or which contain a protected hydroxy or a protected amino function do not possess antibiotic activity to any appreciable degree. However, by removal of the hydroxy and amino function protecting groups, by employing well known methods and procedures, the antibiotic compounds of the invention are obtained where in the Formula I, $R_1$ is hydrogen, and a free amino or free hydroxy group is present.

In the following illustrative examples, infrared absorption spectrum and nuclear magnetic resonance spectrum are abbreviated IR and NMR respectively. Only the significant IR absorption attributable to the carbonyl function of the beta-lactam ring is given. Likewise, the pertinent peaks observed in the NMR spectra are listed. The nuclear magnetic resonance spectra were obtained on a Varian Associated T-60 Spectrometer with tetramethylsilane as the reference standard. The chemical shifts are expressed in $\delta$ values in parts per million (ppm) and coupling constants (J) are expressed as Hz in cycles per second (cps).

The following standard abbreviations are employed for the observed peaks in the NMR spectra: $d$ (doublet), $m$ (multiplet), $p$ (proton) and $s$ (singlet).

I. Preparation of Cephalosporin Michael Adducts

EXAMPLE 1

Preparation of 2,2,2-trichloroethyl 7-acetamido-2-(2,2-dimethoxycarbonylethyl)-3-methyl-3-cephem-4-carboxylate sulfoxide One equivalent of sodium hydride, 0.153 g. (3.18 millimole), as a 50 percent mineral oil dispersion, was added under nitrogen to 0.420 g. (3.18 millimole) of dimethylmalonate in 50 ml. of DMF cooled to −40°C. in an acetone dry-ice bath. The reaction mixture was stirred for about 10 minutes to form the methylene carbanion while the reaction temperature was allowed to warm to about 5°C. Trichloroethyl 7-acetamido-2-methylene-3-methyl-4-carboxylate sulfoxide 1.248 g. (3.0 millimole), in 50 ml. of DMF was added dropwise to the cold (−40°C.) reaction mixture. The reaction was continued for 30 minutes at −30° to −15°C. during which time the reaction mixture became brown. Five milliliters of 1N hydrochloric acid was added dropwise to the reaction which was allowed to warm to 0°C. and the brown color of the reaction changed to light yellow. The reaction mixture was taken up into ethyl acetate. The ethyl acetate phase was washed successively thrice with dilute sodium chloride solution, twice with water and saturated sodium chloride solution. The ethyl acetate solution was dried ($Na_2SO_4$) and evaporated in vacuo to a residue which was chromatographed on silica gel. The residue was chromatographed using ethyl acetate-benzene gradient to yield 1.69 g. of trichloroethyl 7-acetamido-2-(2,2-dimethoxycarbonylethyl)-3-methyl-3-cephem-4-carboxylate sulfoxide which was characterized by physical data.

Mass spectrum, 528 (m/e). The NMR in deuterochloroform showed bands at 2.14 ($CH_3CON$, s, 3p); 2.34 (3—$CH_3$, s, 3p); 1.3–2.9 (2-methylene, m, 2p); 3.5–4.0 (2-methyne + adduct methyne, m, 2p); 3.84 ($CH_3CO_2$, s, 3p); 3.88 ($CH_3CO_2$, s, 3p); 4.7 (H-6, d, J=4.0 Hz, 1p); 4.98 ($Cl_3CCH_2CO_2$, AB, 2p); 6.11 H-7, q, J=4.0, 9.0 Hz, 1p); 7.01 $\delta$ (-NH, d, J=9.0, 1p).

EXAMPLE 2

Preparation of 2,2,2-trichloroethyl 3-methyl-2-(2,2-dicyanoethyl)-7-phenoxyacetamido-3-cephem-4-carboxylate sulfoxide Malononitrile, 140.5 mg. (2.12 millimole), was dissolved in 25 ml. of DMF under nitrogen with stirring and the solution was cooled to −10°C. One equivalent, 101 mg. (2.12 millimole) of sodium hydride as a 50 percent mineral oil dispersion was added in one lot and the reaction was continued at 0°C for about 10 minutes to permit carbanion formation. The reaction mixture was cooled to −30°C. and 1016 mg. (2.00 millimole) of 2,2,2-trichloroethyl 3-methyl-2-methylene-7-phenoxyacetamido-3-cephem-4-carboxylate sulfoxide in 20 ml. of DMF was added dropwise. The reaction was continued at about −20°C. for 30 minutes while the color of the reaction changed to brown. Five milliliters of 1N hydrochloric acid was added dropwise while the temperature rose to 0°C. and the color of the reaction changed to light yellow. The reaction mixture was taken up in ethyl acetate. The ethyl acetate solution was washed successively thrice with water, dilute hydrochloric acid and sodium chloride solution and finally with sodium chloride solution. The ethyl acetate was dried ($Na_2SO_4$) and evaporated in vacuo to a residue. The residue was chromatographed on silica gel using benzene and benzene-ethyl acetate as gradient to yield 919 mg. of 2,2,2-trichloroethyl 3-methyl-2-(2,2-dicyanoethyl)7-phenoxyacetamido-3-cephem-4-carboxylate sulfoxide and 300 mg. of a mixture containing product and starting material. The malononitrile adduct product was characterized by physical data.

The NMR in deuterochloroform showed bands at 1.9–2.5 (adduct methylene, m, 2p); 2.30 (3—$CH_3$, s, 3p); 3.8 (2-methyne, m, 1p); 4.2–4.5 (adduct methyne, m, 1p); 4.60 ($PhOCH_2$, s, 2p); 4.80 (H-6, d, J=4.0 Hz, 1p); 5.06 ($CCL_3CH_2CO_2$, s, 2p); 6.18 (H-7, q, J=4.0, 10.0 Hz, 1p); 7.8 $\delta$ (NH, d, J=10.0 Hz, 1p).

EXAMPLE 3

Preparation of 2,2,2-trichloroethyl 3-acetoxymethyl-2-(2-cyano-2-ethoxycarbonylethyl)-7-[2-(2-thienyl)acetamido]-3-cephem-4-carboxylate sulfoxide One hundred twenty milligrams (1.06 millimole) of ethyl cyanoacetate was dissolved in 10 ml. of DMF under nitrogen with stirring and the solution was cooled to −10°C. Fifty-one milligrams (1.06 millimole) of sodium hydride, as a 50 percent mineral oil dispersion, was added in one lot to the cold reaction mixture. The reaction was continued at 0°C. for about 5 minutes to permit carbanion formation. The reaction was cooled to −10°C. and 556 mg. (1.00 millimole) of 2,2,2-trichloroethyl 3-acetoxymethyl-2-methylene- 7-[2-(2-thienyl)acetamido]-3-cephem-4-carboxylate sulfoxide in 8 ml. of DMF was added dropwise. The reaction was continued for about 1 hour at 0°C. while the color of the reaction became brown. After cooling to −10°C., 2 milliliters of saturated sodium chloride was added. The reaction mixture was taken up in ethyl acetate and washed successively with water until the washings were clear and finally with sodium chloride solution. The ethyl acetate was dried ($Na_2SO_4$) and evaporated in vacuo to a residue. The residue was chromatographed using benzene and benzene-ethyl acetate (1:1) gradient to give 248 mg. of 2,2,2-trichloroethyl 3-acetoxy-2-(2-cyano-2-ethoxycarbonylethyl)-7-[2-(2-thienyl)acetamido]-3-cephem-4-carboxylate sulfoxide which was characterized by physical data.

IR ($CHCl_3$): 1810 cm$^{-1}$ ($\beta$-lactam) The NMR in deuterochloroform showed bands at 1.1–1.5 (ester $CH_3$, m (mixture), 3p); 2.0–2.2 (s(broad), 4p); 3.7–5.2 (m(broad), 11p); 6.15 δ (H-7, q, J=4.0, 10.0 Hz. 1p). The NMR shows a mixture of isomers at C-2 by the mixture of the signals for the ethyl ester (1.1–1.5 δ).

EXAMPLE 4

Preparation of 2,2,2-trichloroethyl 3-acetoxymethyl-2-(2,2-dicyanoethyl)-7-[2-(2-thienyl)acetamido]-3-cephem-4-carboxylate sulfoxide Seventy milligrams (1.06 millimole) of malononitrile, 51 mg. (1.06 millimole) of sodium hydride (50 percent mineral oil dispersion) and 556 mg. (1.00 millimole) of 2,2,2-trichloroethyl 3-acetoxymethyl-2-methylene-7-[2-(2-thienyl)acetamido]-3-cephem-4-carboxylate sulfoxide were reacted by the method of Example 3 to yield 182 mg. of amorphous 2,2,2-trichloroethyl 3-acetoxymethyl-2-(2,2-dicyanoethyl)-7-[2-(2-thienyl)acetamido]-3-cephem -4-carboxylate sulfoxide after chromatography. The NMR of the product in deuterochloroform supports the structure of the product.

EXAMPLE 5

Preparation of 2,2,2-trichloroethyl 2-[2,2-bis(2,2,2-trichloroethoxycarbonyl)ethyl]-3-methyl-7-phenoxyacetamido-3-cephem-4-carboxylate sulfoxide (A) Bis-(2,2,2-trichloroethyl) malonate.

One equivalent of malonic acid, 62.44 g. (0.6 mole), and 179.3 g (1.2 mole) of 2,2,2-trichloroethanol were dissolved in 1 liter of benzene and 8 ml. of concentrated sulfuric acid was added. The reaction mixture was refluxed for 21 hours using a Dean-Stark trap to collect the azeotrope distillate. The reaction mixture was evaporated in vacuo and the residue was taken up in ethyl acetate. The ethyl acetate phase was washed successively thrice with sodium bicarbonate solution, dilute sodium chloride solution and saturated sodium chloride solution, and dried ($Na_2SO_4$). The ethyl acetate was evaporated in vacuo to a residual oil. The oil was distilled and the fraction, bp 132°–142°/0.9 mm, was collected to yield 192 g. of bis-(2,2,2-trichloroethyl)malonate which crystallized upon standing.

(B) 2,2,2-Trichloroethyl 2[2,2-bis-(2,2,2-trichloroethoxycarbonyl)ethyl]-3-methyl-7-phenoxyacetamido-3-cephem-4-carboxylate sulfoxide.

Bis-(2,2,2-trichloroethyl) malonate, 24.2 g. (66 millimole), was dissolved in 600 ml. of DMF under nitrogen and the reaction mixture was cooled to −5°C. One equivalent of sodium hydride, 3.20 g. (66 millimole), as a 50 percent mineral oil dispersion, was added and allowed to react with stirring for one half hour to form the anion. The reaction was cooled to −60°C. and 30.46 g. (60 millimole) of 2,2,2-trichloroethyl 3-methyl-2-methylene-7-phenoxyacetamido-3-cephem- 4-carboxylate sulfoxide dissolved in 500 ml. of DMF was added dropwise to the cold reaction mixture. The reaction was continued for one half hour at about −30°C. The reaction mixture was cooled to −10°C. and 100 ml. of 1N hydrochloric acid was added dropwise resulting in a color change from brown to yellow. The reaction mixture was taken up in ethyl acetate and washed with dilute hydrochloric acid 4 times. The ethyl acetate phase was then washed with water and saturated sodium chloride solution and was dried ($Na_2SO_4$). The ethyl acetate was evaporated in vacuo to a broth residue. The residue was chromatographed on silica gel using benzene-ethyl acetate (1:1) as eluent to yield 50.4 g. of 2,2,2-trichloroethyl 2-[2,2-bis(2,2,2-trichloroethoxycarbonyl)ethyl]-3-methyl-7-phenoxyacetamido-3-cephem-4-carboxylate sulfoxide which was characterized by physical data.

The NMR in deuterochloroform showed bands at 1.5–3.1 (adduct methylene, m, 2p); 2.27 (3.$CH_3$, s, 3p); 3.5–4.2 (2-methyne + adduct methyne, m, 2p); 4.56 ($PhOCH_2$, s, 2p); 4.70 (H-6, d, J=4.0 Hz, 1p); 4.85, 4.90 (two $CCl_3CH_2CO_2$, two s, 4p); 5.00 (4-$CCl_3CH_2CO_2$, s, 2p); 6.20 (H-7, q, J=4.0, 10.0 Hz, 1p); 7.90 δ (NH, d, J=10.0 Hz, 1p).

EXAMPLE 6

Preparation of 2,2,2-trichloroethyl 3-methyl-2-(2-nitroethyl)-7-phenoxyacetamido-3-cephem-4-carboxylate sulfoxide Two millimoles, 1016 mg., of 2,2,2-trichloroethyl 3-methyl-2-methylene-7-phenoxyacetamido-3-cephem-4-carboxylate sulfoxide was dissolved in 30 ml. of nitromethane under nitrogen. The solution was cooled to about −50°C. with stirring and one equivalent, 96 mg. (2.0 millimole), of sodium hydride as a 50 percent mineral oil dispersion was added in one lot. A vigorous reaction occurred. The reaction was continued for 30 minutes at about 5°C. The reaction mixture was decomposed with 10 ml. of 1N hydrochloric acid by dropwise addition. The color of the reaction changed from brown to light yellow. The reaction mixture was taken up in ethyl acetate. The ethyl acetate solution was washed thrice with dilute hydrochloric acid. The ethyl acetate solution was finally washed with saturated sodium chloride solution and dried ($Na_2SO_4$). The ethyl acetate was evaporated in vacuo to a residue. The residue was chromatographed on silica gel using benzene and benzene-ethyl acetate (1:1) gradient to yield 824 mg. of product. The product was crystallized from acetone-dichloromethane-hexane to give 2,2,2-trichloroethyl 3-methyl-2-(2-nitroethyl)-7-phenoxyacetamido-3-cephem-4-carboxylate sulfoxide, mp about 181°–182°C., colorless needles. The yield of product was reduced from 70 percent to about 20 percent when DMF was used as solvent.

Analysis: $C_{20}H_{20}Cl_3N_3O_8S$ MW 568.83. Calc: C, 42.23; H, 3.54; N, 7.39. Found: C, 42.44; H, 3.52; N, 7.63.

The NMR in deuterochloroform showed bands at 1.7–2.5 ($NO_2CH_2CH_2$, m, 2p); 2.1 (3—$CH_3$, s, 3p); 3.6 (2-methyne, m, 1p); 4.4–4.6 ($NO_2CH_2CH_2$, m, 2p); 4.50 ($PhOCH_2$, s, 2p); 4.60 (H-6, d, J=4.0 Hz); 4.86 ($CCl_3Ch_2CO_2$, s, 2p); 6.05 (H-7, q, J=4.0, 11.0 Hz, 1p);

7.89 δ (NH, d, J=11.0 Hz).

The NMR in deuterodimethylsulfoxide showed bands at 1.7–1.9 ($NO_2CH_2CH_2$, m, 2p); 2.2 (3—$CH_3$, s, 3p); 3.95 (2-methyne, m, 1p); 4.6–4.9 ($NO_2CH_2CH_2$, m, 2p); 4.66 ($PhOCH_2$, s, 2p); 5.10 ($Cl_3CH_2CO$, s, 2p); 5.12 (H-6, d, J=4.0 Hz, 1p); 6.05 (H-7, q, J=4.0, 10.0 Hz, 1p); 8.10 δ (NH, d, J=10.0 Hz, 1p).

(II) Preparation of 3-cephem-4-carboxylic acid Michael adducts

EXAMPLE 7

Preparation of 2,2,2-trichloroethyl 2-(2,2-dimethoxycarbonylethyl)-3-methyl-7-phenoxyacetamido-3-cephem-4-carboxylate sulfoxide One equivalent, 8.40 g. (63.6 millimole), of dimethyl malonate was dissolved in 600 ml. of DMF under nitrogen and the mixture was cooled to −40°C. Sodium hydride, 3.08 g. (63.6 millimole), as a 50 percent mineral oil dispersion, was added with stirring and the reaction was continued for about 30 minutes at 0°C. to allow carbanion formation. The reaction mixture was again cooled (−50°C.) and trichloroethyl 3-methyl-2-methylene-7-phenoxyacetamido-3-cephem-4-carboxylate sulfoxide, 30.468 g. (6.0 millimole), in 500 ml. of DMF was added dropwise. The reaction was continued for 30 minutes in the cold (−30°C.). The reaction mixture was allowed to warm up to about −5°C. and 100 ml. of 1N hydrochloric acid was added dropwise causing a color change from brown to light yellow. After the temperature reached 0°C., the reaction mixture was taken up in ethyl acetate. The ethyl acetate phase was washed successively thrice with dilute hydrochloric acid and then with saturated sodium chloride solution. The ethyl acetate solution was dried ($Na_2SO_4$) and evaporated in vacuo to a residue. The residue was chromatographed on silica gel using benzene-ethyl acetate gradient to yield 35.7 g. of trichloroethyl 2-(2,2-dimethoxycarbonylethyl)-3-methyl-7-phenoxyacetamido-3-cephem-4-carboxylate sulfoxide which was characterized by physical data.

Mass spectrum showed a peak at 622 (m/e), m-16. IR ($CHCl_3$): 1805 (β-lactam) and 1055 $cm^{-1}$ (sulfoxide). NMR in deuterochloroform showed bands at 1.5–1.9, 2.18–2.70 (methylene adduct, m, 2p); 2.27 (3—$CH_3$, s, 3p); 3.5–3.7 (2-methyne + adduct methyne, m, 2p); 3.80 ($CH_3CO_2$, s, 3p); 3.91 ($CH_3CO_2$, s, 3p); 4.58 ($PhOCH_2$, s, 2); 4.68 (H-6, d, J=5.0 Hz, 1p); 4.89, 5.03 ($Cl_3CCH_2$, AB, J=12.0 Hz, 2p); 6.23 (H-7, q, J=5.0, 10.0 Hz, 1p); 7.91 δ (NH, d, J=10.0 Hz, 1p).

EXAMPLE 8

Preparation of 2,2,2-trichloroethyl 2-(2,2-dimethoxycarbonylethyl)-3-methyl-7-phenoxyacetamido-3-cephem-4-carboxylate Four hundred and forty-nine milligrams (0.702 millimole) of trichloroethyl 2-(dimethyl methylenemalonate)-3-methyl-7-phenoxyacetamido-3-cephem-4-carboxylate sulfoxide was dissolved in 15 ml. of DMF and the solution was cooled (5°C.). Phosphorous trichloride, 0.615 ml., was added to the cold reaction mixture which was stirred for 1 hour while the mixture was allowed to come to room temperature. The reaction mixture was taken up in ethyl acetate. The ethyl acetate solution was washed successively thrice with water and saturated sodium chloride solution. The ethyl acetate solution was dried ($Na_2SO_4$) and evaporated in vacuo to an oily residue. The oil was chromatographed on silica gel using benzene-ethyl acetate gradient to yield 345 mg. of 2,2,2-trichloro 2-(2,2-dimethoxycarbonylethyl)-3-methyl-7-phenoxyacetamido-3-cephem-4-carboxylate which was characterized by physical data.

IR ($CHCl_3$): 1790 (β-lactam).

NMR in deuterochloroform showed bands at 1.7–2.9 (methylene adduct, m, 2p); 2.25 (3—$CH_3$, s, 3p); 3.2–3.9 (2 methyne + adduct methyne, m, 2p); 3.77 (2 $CH_3CO_2$, two s, 6p); 4.56 ($PhOCH_2$, s, 2p); 4.91 (H-6, d, J=5.0 Hz, 1p); 5.0 ($CCl_3Ch_2CO_2$, AB, 2p); 5.92 δ (H-7, q, J=5.0, 9.0 Hz, 1p).

EXAMPLE 9

2-(2,2-Dimethoxycarbonylethyl)-3-methyl-7-phenoxyacetamido-3-cephem-4-carboxylic acid The reaction solvent was prepared by mixing 30 ml. of DMF and 5 ml. of acetic acid. Three hundred and forty-five milligrams of trichloroethyl 2-(dimethyl methylenemalonate)-3-methyl-7-phenoxyacetamido-3-cephem-4-carboxylate was dissolved in 20 ml. of the DMF-acetic acid solvent and the reaction mixture was cooled to 5°C. Zinc dust, 345 mg., was added to the cold reaction mixture and the reaction was stirred for 1 hour. The zinc dust was filtered using ethyl acetate as a wash solvent. The filtrate was twice extracted with sodium bicarbonate solution. The basic aqueous phase was layered with ethyl acetate and acidified with 1N hydrochloric acid. The acid product was extracted into the ethyl acetate. The ethyl acetate phase was washed with saturated sodium chloride solution and dried ($Na_2SO_4$). The ethyl acetate was evaporated in vacuo to yield 194 mg. of 2-(2,2-dimethoxycarbonylethyl)-3-methyl-7-phenoxyacetamido-3-cephem-4-carboxylic acid which was characterized by physical data.

NMR in deuterochloroform showed bands at 2.2 (3—$CH_3$, s, 3p); 3.4 (2-methyne + adduct methyne, m, 2p); 3.9 (two $CH_3CO_2$, 6p); 4.5 ($PhOCH_2$, s, 2p); 5.0 (H-6, d, 1p); 5.9 δ (H-7, q, 1p).

EXAMPLE 10

Preparation of 2,2,2-trichloroethyl 3-acetoxymethyl-2-(2,2-dimethoxycarbonylethyl)-7-[2-(2-thienyl)acetamido]-3-cephem-4-carboxylate sulfoxide One hundred forty milligrams (1.06 millimole) of dimethyl malonate was dissolved in 10 ml. of DMF under nitrogen and cooled to about −10°C. with stirring. One equivalent, 51 milligrams (1.06 millimole), of sodium hydride, as a 50 percent mineral oil dispersion was added in one lot to the cold reaction mixture. The reaction was continued for about 10 minutes at 0°C. to permit carbanion formation. The reaction mixture was cooled to about −10°C. and 556 mg. (1.0 millimole) of 2,2,2-trichloroethyl 3-acetoxy-2-methylene-7-[2-(2-thienyl)acetamido]-3-cephem-4-carboxylate sulfoxide in 10 ml. of DMF was added dropwise. The reaction was continued for about 1 hour at 5°C. and the color of the mixture changed to brown. Three milliliters of saturated sodium chloride was added dropwise to the cold (−10°C.) reaction mixture. The reaction mixture was taken up in ethyl acetate. The ethyl acetate solution was washed with water until the washings were clear and then given a final wash with sodium chloride solution. The ethyl acetate was dried ($Na_2SO_4$) and evaporated in vacuo to an oily residue. The residue was chromatographed on silica gel using benzene ethyl-acetate gradient to yield 405 mg. of 2,2,2-trichloroethyl 3-acetoxy-2-(2,2-dimethoxycarbonylethyl)-7-[2-(2-thienyl)acetamido]-3-cephem-4-carboxylate sulfoxide which was characterized by physical data.

IR (CHCl$_3$): 1816 ($\beta$-lactam), 1750, 1055 cm$^{-1}$ (sulfoxide)

The NMR in deuterochloroform showed bands at 1.2–3.0 (adduct methylene, m, 2p); 2.10 (CH$_3$CO, s, 3p); 3.4–4.1 (thiophene methylene, adduct methyne, 2-methyne, m, 4p); 4.6–5.2 (CCl$_3$CH$_2$, CH$_2$OAC, H-6, m, 5p); 6.18 $\delta$ (H-7, q, J=5.0, 10.0 Hz, 1p).

EXAMPLE 11

Preparation of 2,2,2-trichloroethyl 3-acetoxymethyl-2-(2,2-dimethoxycarbonylethyl)-7-[2-(2-thienyl)acetamido]-3-cephem-4-carboxylate Four hundred and five milligrams (0.590 millimole) of 2,2,2-trichloroethyl 3-acetoxymethyl-2-(2,2-dimethoxycarbonylethyl)-7-[2-(2-thienyl)acetamido]-3-cephem-4-carboxylate sulfoxide were dissolved in 15 ml. of DMF and the solution was cooled to about $-5°$C. Ten equivalents, 0.515 ml. (5.90 millimole), of phosphorous trichloride were added dropwise to the reaction mixture and the reaction was continued for 1 hour without further cooling. During this period the reaction turned brown. The reaction mixture was taken up in ethyl acetate. The ethyl acetate solution was washed successively four times with water and once with sodium chloride solution and was dried (Na$_2$SO$_4$). The ethyl acetate was evaporated in vacuo to a residue. The residue was chromatographed on silica gel using benzene and benzene-ethyl acetate gradient to yield 230 mg. of 2,2,2-trichloroethyl 3-acetoxymethyl-2-(2,2-dimethoxycarbonylethyl)-7-[2-(2-thienyl)acetamido]-3-cephem-4-carboxylate which was characterized by physical data.

IR (CHCl$_3$): 1795 ($\beta$-lactam)

The NMR in deuterochloroform showed bands at 1.2–2.8 (adduct methylene, m, 2p); 2.10 (3-CH$_3$CO$_2$, s, 3p); 3.5–4.0 (thiophene methylene, adduct methyne, adduct CH$_3$CO$_2$ (two), 2-methyne, m, 10p); 4.6–5.2 (CCl$_3$CH$_2$CO$_2$, CH$_2$OAC, H-6, m, 5p); 5.90 (H-7, q, J=4.0, 9.0 Hz, 1p); 6.45 $\delta$ (NH, d, J=9.0 Hz, 1p).

EXAMPLE 12

Preparation of 3-acetoxymethyl-2-(2,2-dimethoxycarbonylethyl7-[2-(2-thienyl)acetamido]-3-cephem-4-carboxylic acid Two hundred-thirty milligrams (0.342 millimole) of 2,2,2-trichloroethyl 3-acetoxymethyl-2-(dimethyl methylenemalonate)-7-[2-(2-thienyl)acetamido]-3-cephem-4-carboxylate was dissolved in 20 ml. of reaction solvent prepared by mixing 30 ml. of DMF and 5 ml. of glacial acetic acid. The solution was cooled ($-5°$C.) with stirring and 230 mg. of zinc dust was added in one lot. The reaction was continued for about 1 hour without further cooling. The reaction mixture was taken up in ethyl acetate and the zinc dust was filtered using ethyl acetate as a wash. The ethyl acetate solution was extracted twice with sodium bicarbonate solution. The basic aqueous phase was layered with ethyl acetate and acidified with 1N hydrochloric acid. The acid product was extracted into the ethyl acetate. The ethyl acetate phase was washed with sodium chloride solution and dried (Na$_2$SO$_4$). The ethyl acetate was evaporated in vacuo to yield 73 mg. of 3-acetoxymethyl-2-(2,2-dimethoxycarbonylethyl)-7-[2-(2-thienyl)acetamido]-3-cephem-4-carboxylic acid which was characterized by physical data.

IR (CHCl$_3$): 1790 cm$^{-1}$ ($\beta$-lactam)

The NMR in deuterochloroform showed bands at 2.13 (3-CH$_3$CO$_2$, s, 3p); 3.6–3.9 (adduct methyne, adduct CH$_3$CO$_2$ (two), thiophene methylene, 2-methyne, m, 10p); 5.0 (H-6, CH$_2$OAC, m, 3p); 5.9 $\delta$ (H-7, m, 1p).

EXAMPLE 13

Preparation of 2,2,2-trichloroethyl 3-acetoxymethyl-2-(2-acetyl-2-ethoxycarbonylethyl)-7-[2-(2-thienyl)acetamido]-3-cephem-4-carboxylate sulfoxide One hundred thirty-eight milligrams (1.06 millimole) of ethyl acetoacetate was dissolved in 10 ml. of DMF under nitrogen and the stirred solution was cooled to $-10°$C. One equivalent, 51 mg. (1.06 millimole) of sodium hydride, as a 50 percent mineral oil dispersion, was added in one lot. The reaction was continued for about 5 minutes at 0°C. to permit carbanion formation. Five hundred fifty-six milligrams (1.00 millimole) of 2,2,2-trichloroethyl 3-acetoxymethyl-7-[2-(2-thienyl)acetamido]-3-cephem-4-carboxylate sulfoxide in 15 ml. of DMF was added dropwise to the cold ($-10°$C.) reaction mixture. The reaction was continued 1 hour at 0°C. Two milliliters of saturated sodium chloride was added at $-10°$C. and the reaction was stirred for about 5 minutes without further cooling. The reaction mixture was taken up in ethyl acetate and washed with dilute sodium chloride solution until the washings were clear and then given a final washing with saturated sodium chloride solution. The ethyl acetate was dried (Na$_2$SO$_4$) and evaporated in vacuo to a residue. The residue was chromatographed on silica gel using benzene-ethyl acetate gradient to yield 481 mg. of 2,2,2-trichloroethyl 3-acetoxymethyl-2-(2-acetyl-2-ethoxycarbonylethyl)-7-[2-(2-thienyl)acetamido]-3-cephem-4-carboxylate sulfoxide which was characterized by physical data.

IR (CHCl$_3$): 1810 ($\beta$ lactam), 1055 cm$^{-1}$ (sulfoxide).

The NMR in deuterochloroform showed bands at 1.3 (ester CH$_3$, m (triplet mixture), 3p); 2.01 (CH$_3$CO$_2$, s, 3p); 2.3 (CH$_3$CO, s, 3p); 4.2 (ester methylene, q (mixture), 2p); 6.3 $\delta$ (H-7, q, J=5.0, 10.0 Hz, 1p). The NMR shows a mixture of isomers at C-2 judged by the mixture of the signals (1.3, 4.22 $\delta$) for the ethyl ester.

EXAMPLE 14

Preparation of 2,2,2-trichloroethyl 3-acetoxymethyl-2-(2-acetyl-2-ethoxycarbonylethyl)-7-[2-(2-thienyl)acetamido]-3-cephem-4-carboxylate.

Four hundred forty-seven milligrams (0.650 millimole) of 2,2,2-trichloroethyl 3-acetoxymethyl-2-(ethyl methyleneacetoacetate)-7-[2-(2-thienyl)acetamido)-3-cephem-4-carboxylate sulfoxide was dissolved in 15 ml. of DMF and the solution was cooled to about 5°C. Phosphorous trichloride, 0.57 ml., was added dropwise to the reaction mixture and the reaction was continued without further cooling for about 1 hour. The reaction mixture was taken up in ethyl acetate and washed successively thrice with water and once with saturated sodium chloride solution and was dried (Na$_2$SO$_4$). The ethyl acetate was evaporated in vacuo to a residue. The residue was chromatographed on silica gel using benzene ethyl-acetate as gradient to provide 324 mg. of 2,2,2-trichloroethyl 3-acetoxymethyl-2-(2-acetyl-2-ethoxycarbonylethyl)-7-[2-(2-thienyl)acetamido]3-cephem-4-carboxylate which was characterized by physical data.

IR (CHCl$_3$): 1794 cm$^{-1}$ ($\beta$-lactam)

The NMR in deuterochloroform showed bands at 1.2 (ester CH$_3$, m (triplet, mixture), 3p); 2.07, 2.30 (CH$_3$CO, CH$_3$CO$_2$, s, (two), 6p); 4.2 (ester methylene, q (mixture), 2p); 5.90 (H-7, q. J=5.0, 8.0 Hz, 1p); 6.44 $\delta$ (NH, d, J=8.0 Hz, 1p). The NMR shows a mixture of isomers at C-2 judged by the mixture of the signals (1.2, 1.4 $\delta$) for the ethyl ester.

EXAMPLE 15

Preparation of 3-acetoxymethyl-2-(2-acetyl-2-ethoxycarbonylethyl)-7-[2-(thienyl)acetamido]-3-cephem-4-carboxylic acid Three hundred twenty milligrams (0.478 millimole) of 2,2,2-trichloroethyl 3-acetoxymethyl-2-(ethyl methyleneacetoacetate)-7-[2-(2-thienyl)acetamido]-3-cephem-4-carboxylate was dissolved in 20 ml. of solvent prepared by mixing 30 ml. of DMF and 5 ml. of glacial acetic acid and the solution was cooled to about 5°C. Ten equivalents, 320 mg. (4.89 millimole), of zinc dust was added in one lot and the reaction was continued for about 1 hour in the cold. The reaction mixture was taken up in ethyl acetate and the zinc dust was filtered using ethyl acetate as a wash. The ethyl acetate was extracted thrice with sodium bicarbonate solution. The ethyl acetate phase was washed with sodium chloride solution and dried (Na$_2$SO$_4$). Evaporation of the ethyl acetate in vacuo gave 228 mg. of starting material. The basic aqueous phase was layered with ethyl acetate and acidified with 1N hydrochloric acid. The acid product was extracted into the ethyl acetate. The ethyl acetate extract was washed with sodium chloride solution and dried (Na$_2$SO$_4$). The ethyl acetate was evaporated in vacuo to yield 74 mg. of 3-acetoxymethyl-2-(2-acetyl-2-ethoxycarbonylethyl)-7-[2-(2-thienyl)acetamido]-3-cephem-4-carboxylic acid which was characterized by physical data.

The NMR in deuterochloroform showed bands at 1.3 (ester CH$_3$, m (triplet mixture), 3p); 2.07, 2.30 (CH$_3$CO$_2$, CH$_3$CO, s (two), 6p); 4.2 (ester methylene, q (mixture), 2p); 5.90 $\delta$ (H-7). The NMR shows a mixture of C-2 isomers as judged by the mixture of the signals for the ethyl ester (1.3, 4.2 $\delta$).

I claim:
1. A compound of the formula

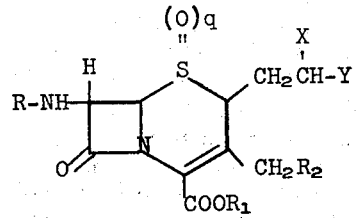

wherein
R is hydrogen, C$_1$-C$_8$ alkanoyl, benzoyl, or a group represented by the formula:

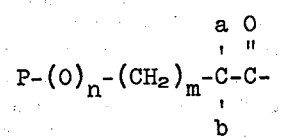

wherein
P is 2-thienyl, 3-thienyl, 2-furyl, 3-furyl, phenyl or phenyl substituted by amino, protected amino, halogen, hydroxy, protected hydroxy, C$_1$-C$_4$ lower alkyl, or C$_1$-C$_4$ lower alkoxy;
$a$ is hydrogen or C$_1$-C$_3$ alkyl;
$b$ is hydrogen, C$_1$-C$_3$ alkyl, amino, protected amino, hydroxy, or protected hydroxy;
$m$ is 0 or an integer from 1 to 3;
$n$ is 0 or 1;
subject to the limitation that when
$n$ is 1,
$p$ is phenyl or phenyl substituted by amino, protected amino, halogen, hydroxy, protected hydroxy, C$_1$-C$_4$ lower alkyl or C$_1$-C$_4$ lower alkoxy; and
$b$ is hydrogen or C$_1$-C$_3$ alkyl;
R$_1$ is hydrogen, a carboxylic acid protecting group, or an alkali metal or alkaline earth metal cation;
R$_2$ is hydrogen, C$_2$-C$_5$ alkanoyloxy, or C$_1$-C$_4$ alkoxy;
$q$ is 0 or 1; and
X and Y are independently hydrogen, acetyl, benzoyl, carboethoxy, carbomethoxy, cyano, nitro and 2,2,2-trichlorocarboethoxy;
subject to the limitations that when one of X and Y is hydrogen, the other is cyano or nitro.

2. A compound as defined in claim 1 wherein $q$ is 1.

3. A compound as defined in claim 2, said compound being 2,2,2-trichloroethyl 3-acetoxymethyl 2-(2,2-dimethoxycarbonylethyl)-7-[2-(2-thienyl)acetamido]-3-cephem-4-carboxylate sulfoxide.

4. A compound as defined in claim 2, said compound being 2,2,2-trichloroethyl 3-acetoxymethyl 2-(2-acetyl-2-ethoxycarbonylethyl)-7-[2-(2-thienyl)acetamido]-3-cephem-4-carboxylate sulfoxide.

5. A compound as defined in claim 2, said compound being p-nitrobenzyl 2-(2,2-dimethoxycarbonylethyl)-3-methyl-7-phenoxyacetamido-3-cephem-4-carboxylate sulfoxide.

6. A compound as defined in claim 2, said compound being 2,2,2-trichloroethyl 2-(2,2-dimethoxycarbonylethyl)3-methyl-7-phenoxyacetamido-3-cephem-4-carboxylate sulfoxide.

7. A compound as defined in claim 1 wherein $q$ is 0.

8. A compound as defined in claim 7, said compound being 3-acetoxymethyl-2-(2,2-dimethoxycarbonylethyl)-7-[2-(2-thienyl)acetamido]-3-cephem-4-carboxylic acid.

9. A compound as defined in claim 7, said compound being 3-acetoxymethyl-2-(2-acetyl-2-ethoxycarbonylethyl)-7-[2-(2-thienyl)acetamido]-3-cephem-4-carboxylic acid.

10. A compound as defined in claim 7, said compound being 2-(2,2-dimethoxycarbonylethyl)-3-methyl-7-phenoxyacetamido3-cephem-4-carboxylic acid.

11. The process for preparing the compound of claim 1, wherein $q$ is 1 and R and R$_1$ are groups other than hydrogen, which comprises reacting in a substantially anhydrous inert solvent at a temperature between −40°C, and 20°C. a carbanion of the formula -CHXY, wherein X and Y are independently hydrogen, acetyl, benzoyl, carboethoxy, carbomethoxy, cyano, nitro, or 2,2,2-trichlorocarboethoxy with the limitation that when one of X or Y is hydrogen, the other is cyano or nitro, with a compound of the formula

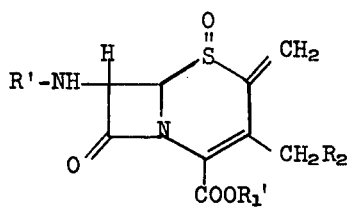

wherein
R' is $C_1$-$C_8$ alkanoyl, benzoyl, or a group represented by the formula:

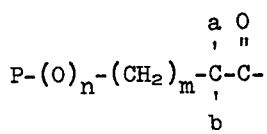

wherein

P is 2-thienyl, 3-thienyl, 2-furyl, 3-furyl, phenyl or phenyl substituted by amino, protected amino, halogen, hydroxy, protected hydroxy, $C_1$-$C_4$ lower alkyl, or $C_1$-$C_4$ lower alkoxy;

a is hydrogen or $C_1$-$C_3$ alkyl;

b is hydrogen, $C_1$-$C_3$ alkyl, amino, protected amino, hydroxy, or protected hydroxy;

m is 0 or an integer from 1 to 3;

n is 0 or 1;

subject to the limitation that when n is 1, p is phenyl or phenyl substituted by amino, protected amino, halogen, hydroxy, protected hydroxy, $C_1$-$C_4$ lower alkyl, or $C_1$-$C_4$ lower alkoxy; and b is hydrogen or $C_1$-$C_3$ alkyl;

$R_1'$ is a carboxylic acid protecting group or an alkali metal or alkaline earth metal cation; and $R_2$ is hydrogen, $C_2$-$C_5$ alkanoyloxy, or $C_1$-$C_4$ alkoxy.

12. The process of claim 11 wherein $R_2$ is hydrogen.

13. The process of claim 12 wherein R' is phenoxyacetyl, $R_1'$ is 2,2,2-trichloroethyl, X and Y are 2,2,2-trichlorocarboethoxy.

* * * * *